(12) United States Patent
Sailor et al.

(10) Patent No.: US 7,759,129 B2
(45) Date of Patent: Jul. 20, 2010

(54) OPTICAL SENSOR FOR DETECTING CHEMICAL REACTION ACTIVITY

(75) Inventors: Michael J. Sailor, La Jolla, CA (US);
Manuel M. Orosco, La Jolla, CA (US);
Claudia Pacholski, Stuttgart (DE);
Gordon M. Miskelly, Avondale (NZ)

(73) Assignee: The Regents of the University of California, Oakland, CA (US)

( * ) Notice: Subject to any disclaimer, the term of this patent is extended or adjusted under 35 U.S.C. 154(b) by 8 days.

(21) Appl. No.: 12/087,691

(22) PCT Filed: Jan. 10, 2007

(86) PCT No.: PCT/US2007/000912

§ 371 (c)(1),
(2), (4) Date: Dec. 16, 2008

(87) PCT Pub. No.: WO2007/082075

PCT Pub. Date: Jul. 19, 2007

(65) Prior Publication Data

US 2009/0215191 A1 Aug. 27, 2009

Related U.S. Application Data

(60) Provisional application No. 60/757,958, filed on Jan. 11, 2006.

(51) Int. Cl.
*G01N 21/00* (2006.01)

(52) U.S. Cl. .................. 436/164; 436/165; 436/518; 436/527; 436/805; 356/345; 356/352; 385/12; 385/129; 385/130; 422/52.05; 422/82.11; 435/287.1; 435/287.2; 435/288.7; 435/808; 435/973

(58) Field of Classification Search ............... None
See application file for complete search history.

(56) References Cited

U.S. PATENT DOCUMENTS

| 6,248,539 B1 | 6/2001 | Ghadiri et al. |
| 7,042,570 B2 | 5/2006 | Sailor et al. |
| 7,318,903 B2 | 1/2008 | Link et al. |

(Continued)

OTHER PUBLICATIONS

Anson, M.L., "The estimation of pepsin, trypsin, papin, and cathepin with hemoglobin", *The Journal of General Physiology*, vol. 22, pp. 79-89 (1938).

(Continued)

*Primary Examiner*—Yelena G Gakh
*Assistant Examiner*—Robert Xu
(74) *Attorney, Agent, or Firm*—Greer, Burns & Crain Ltd.

(57) ABSTRACT

The invention provides an optical sensor for detecting chemical reaction activity, including, e.g., enzyme activity and catalytic or reactive molecule activity. An optical sensor of the invention includes a porous photonic film that produces a predetermined spectral reflectance response. In preferred embodiments, the film has a chemical coating (such as a hydrophobic layer) within its pores with an affinity for the reaction product(s) of the catalytic or otherwise reactive analyte A coating can also act as a protective layer in preferred embodiment. A thin substrate susceptible to reaction by at least one analyte of interest is on the surface of the thin film to block pores of the thin film. A method of detecting chemical reaction activity of the invention exposes the optical sensor to an analyte of interest, such as an enzyme or otherwise catalytic or reactive molecule. The optical sensor is subjected to light and the reflectivity spectrum of the optical sensor is monitored for a change indicative of reaction activity. Monitoring can include observation for a visible change or data acquisition via instruments such as a spectrometer for monitoring for a change in interferometric reflectance spectra.

19 Claims, 5 Drawing Sheets

U.S. PATENT DOCUMENTS

| | | |
|---|---|---|
| 2001/0044119 A1 | 11/2001 | Ghadiri et al. |
| 2002/0072116 A1 | 6/2002 | Bhatia et al. |
| 2002/0192680 A1 | 12/2002 | Chan et al. |
| 2003/0146109 A1 | 8/2003 | Sailor et al. |
| 2004/0152135 A1 | 8/2004 | Ghadiri et al. |
| 2004/0171143 A1 | 9/2004 | Chin et al. |
| 2004/0244889 A1 | 12/2004 | Sailor et al. |
| 2005/0009374 A1 | 1/2005 | Gao et al. |
| 2005/0019799 A1 | 1/2005 | Grasso et al. |
| 2005/0042764 A1 | 2/2005 | Sailor et al. |
| 2005/0101026 A1 | 5/2005 | Sailor et al. |
| 2006/0051872 A1 | 3/2006 | Sailor et al. |
| 2006/0105043 A1 | 5/2006 | Sailor et al. |
| 2006/0236436 A1 | 10/2006 | Li et al. |
| 2006/0255008 A1 | 11/2006 | Link |
| 2007/0051815 A1 | 3/2007 | Sailor et al. |
| 2007/0108465 A1 | 5/2007 | Pacholski |
| 2007/0148695 A1 | 6/2007 | Sailor et al. |
| 2008/0145513 A1 | 6/2008 | Li et al. |

OTHER PUBLICATIONS

Chan, S., Fauchet, P.M., Li, Y., Rothberg, L.J. & Miller, B.L., "Porous silicon microcavities for biosensing applications", *Phys. Status Solidi A*, vol. 182, pp. 541-546 (2000).

Chan, S., Homer, S.R., Miller, B.L. & Fauchet, P.M., "Identification of gram negative bacteria using nanoscale silicon microcavities", *J. Am. Chem. Soc.* vol. 123, pp. 11797-11798 (2001).

Folin, O., Ciocalteu, V. "On tryrosine and tryptophane determinations in proteins", *The Journal of Biological Chemistry*, vol. 73, pp. 627-650 (1927).

Jones, L.J. et al., "Quenched BODIPY dye-labeled casein substrates for the assay of protease activity by direct fluorescence measurement", *Analytical Biochemistry*, vol. 251, pp. 144-152 (1997).

Wang, Q., Wang, J., Geil, P. H., Padua, G. W., "Zein absorption by hydrophilic andhydrophobic surfaces investigated by surface plasmon resonance", *Biomacromolecules*, vol. 5, pp. 356-1361 (2004).

Wiesner, R. & Troll, W., "A new assay for proteases using fluorescent labeling of proteins", *Analytical Biochemistry*, vol. 121, pp. 290-294 (1982).

Zangooie, S., Jansson, R. & Arwin, H., "Ellipsometric characterization of anisotropic porous silicon Fabry-Perot filters and investigation of temperature effects on capillary condensation efficiency", *Journal of Applied Physics*, vol. 86, pp. 850-858 (1999).

PDQ™ Protease Assay Product Data Sheet, Catalog Nos. 0201-0202, No. 10.

OPTICAL SENSOR FOR DETECTING CHEMICAL REACTION ACTIVITY

PRIORITY CLAIM

Applicants claim priority benefits under 35 U.S.C. §119 on the basis of Patent Application No. 60/757,958, filed Jan. 11, 2006.

STATEMENT OF GOVERNMENT INTEREST

This invention was made with government support under Grant No. F49620-02-1-0288 awarded by Air Force Office of Scientific Research. The government has certain rights in the invention.

FIELD OF THE INVENTION

A field of the invention is optical nanostructures, the synthesis of optical nanostructures, and the use of optical nanostructures in sensing applications. Chemical reaction activity, including enzyme activity and the activity of otherwise catalytic or reactive molecules can be detected with sensors and methods of the invention, enabling numerous important sensing applications including biosensing applications such as protease activity detection, screening for cellulases and other carbohydrate-hydrolysing enzymes, and detection of otherwise catalytic or reactive molecules.

BACKGROUND OF THE INVENTION

Detection, analysis and quantification of an analyte, such as a cell, macromolecule, protein, polymer, biomolecule, biopolymer or other molecular complex has widespread application in fields such as genomics, proteomics, drug discovery, medical diagnostics, environmental sensing, pollution monitoring, detection of chemical or biological warfare agents, and industrial process monitoring. For example, cell and tissue-based biosensors are useful for many medical, pharmaceutical, and environmental applications. One significant advantage of using living elements in sensors is that, in principle, complex biological interactions can be monitored. However, many biological events that signal changes in cellular physiology cannot readily be converted into an electronic signal in real-time.

Chemical reactions can signal the occurrence of many events of interest. The reaction activity of enzymes and otherwise catalytic or reactive molecules signals many important biological and non-biological reactions, for example. Such reactions are of interest to researchers to understand and quantify many biological, genetic, and general chemical processes. Research in many fields, including medical, biological, military, and industrial fields seeks to better understand, recognize and quantify the activity of enzymes or otherwise catalytic or reactive molecules.

Protease research is one such field. Proteases are enzymes that break peptide bonds between amino acids of proteins. The activity of proteases is an indicator of many biological processes. Protease activity is therefore a widespread area of research. Protease activity can quickly degrade cells, and is regulated by protease inhibitors. Promoting protease activity to target certain cells, e.g., tumor cells, is one area of research. Inhibiting protease activity to prevent harmful cell destruction such as in HIV research is another area of intense research. As proteases are included in every living cell, the conditional activation and inhibition of protease activity holds great promise in many areas of biological and genetic research.

There is a need for quick assays of protease activity because of their pivotal intra- and inter-cellular role in biological systems. Schemes to quantify protease activity primarily involve either fluorescent or colorimetric assays that are time-consuming and that require relatively large quantities of enzyme. In addition, these assays use substrates that have been modified from their native forms in order to incorporate the relevant indicator chemistries. A typical colorimetric assay, such as from Athena Enzyme systems, requires incubation times up to twenty four hours.

A standard method to detect protease activity uses a fluorescent molecule conjugated to casein or bovine serum albumin substrates. Some concerns with using fluorescent-conjugated substrates are that the presence of the dye may affect the proteolytic cleavage rate, quantification requires a sensitive fluorimeter, and the reagents are costly. The well-known colorimetric assay using the Folin-Ciocalteu reagent operates on native substrates, but it is less sensitive than fluorescence methods and requires an extensive workup procedure.

Research efforts and progress are slowed by such typical conventional methods for detecting protease activity. Relatively large quantities of time and reagents are required, costs can be high, and procedures can be complicated.

The intensity of a porous thin film's visible photoluminescence, e.g., porous silicon, changes depending upon the types of gases absorbed to its surface. This phenomenon constitutes the basis for a simple and inexpensive chemical sensor device. See, U.S. Pat. No. 5,338,415. Porous thin films, e.g., porous silicon, insulator and semiconductor films, can be fabricated to display well-resolved Fabry-Perot fringes in their luminescence and reflection spectra. Such interference-based spectra are sensitive to gases or liquids adsorbed to the inner surfaces of the porous Si layer. See, U.S. Pat. No. 5,318,676, which uses the interference based spectra to identify adsorbed individual gases or liquids. See also, U.S. Pat. No. 6,248,539 used a binder to bind analytes in pores and then identify the analytes by detecting a shift in the reflection spectra. Porous films and particles for sensing are also discussed in U.S. Published Application No. 20060255008, published Nov. 16, 2006, and entitled Photonic Sensor Particles and Fabrication Methods, which discloses use of optical particles in sensing applications, and methods of fabricating optical particles that can target a desired analyte. Strategies for encoding porous films are also discussed in the following U.S. Published Applications: 20060236436, published Oct. 19, 2006 and entitled Nanostructured Casting of Organic and Bio-Polymers in Porous Silicon Templates; 20060105043, published May 18, 2006 and entitled Porous Nanostructures and Methods involving the same; 20050042764, published Feb. 24, 2005 and entitled Optically Encoded Particles; 20050009374, published Jan. 13, 2005 and entitled Direct Patterning of Silicon by Photoelectrochemical Etching; 20040152135, published Aug. 4, 2004 and entitled Porous Semiconductor-Based Optical Interferometric Sensor; and 20030146109, published Aug. 7, 2003 and entitled Porous thin film time-varying reflectivity analysis of samples. Also see U.S. Pat. Nos. 6,897,965, 6,720,177, and 6,248,539, which disclose semiconductor based optical interferometric sensors and discuss fabrication of the same.

SUMMARY OF THE INVENTION

The invention provides an optical sensor for detecting chemical reaction activity, including, e.g., enzyme activity and otherwise catalytic or reactive molecule activity. An optical sensor of the invention includes a porous photonic film that produces a predetermined spectral reflectance response.

In preferred embodiments, the film has a chemical coating (such as a hydrophobic layer) within its pores with an affinity for the reaction product(s) of the catalytic or otherwise reactive analyte A coating can also act as a protective layer in preferred embodiments. A thin substrate susceptible to reaction by at least one analyte of interest is on the surface of the thin film to block pores of the thin film. A method of detecting chemical reaction activity of the invention exposes the optical sensor to an analyte of interest, such as an enzyme or otherwise catalytic or reactive molecule. The optical sensor is subjected to light and the reflectivity spectrum of the optical sensor is monitored for a change indicative of reaction activity. Monitoring can include observation for a visible change or data acquisition via instruments such as a spectrometer for monitoring for a change in interferometric reflectance spectra.

The invention can be used to detect any analyte that can degrade a substrate layer on top of a porous optical sensor having a predetermined optical response so long as the substrate, analyte and sample matrix are excluded by the pores prior to reaction and permit penetration of solution and/or reaction products into the pores, or a reduction in molecular weight of the porous film after reaction. Example analytes include enzymes, such as proteases, and other catalytic and noncatalytic molecules that cause a degradation, cleavage, or other decrease in molecular weight of the substrate susceptible to reaction. Example substrates susceptible to reaction include proteins, RNA, DNA, or macromolecular substrates of hydrolytic enzymes. The affinity coating can be a hydrophobic coating, for example, or an appropriate one of a DNA, RNA, organic oligomers or polymers, metal or nonmetal oxides, or metals

DETAILED DESCRIPTION OF THE PREFERRED EMBODIMENTS

Figure 1:
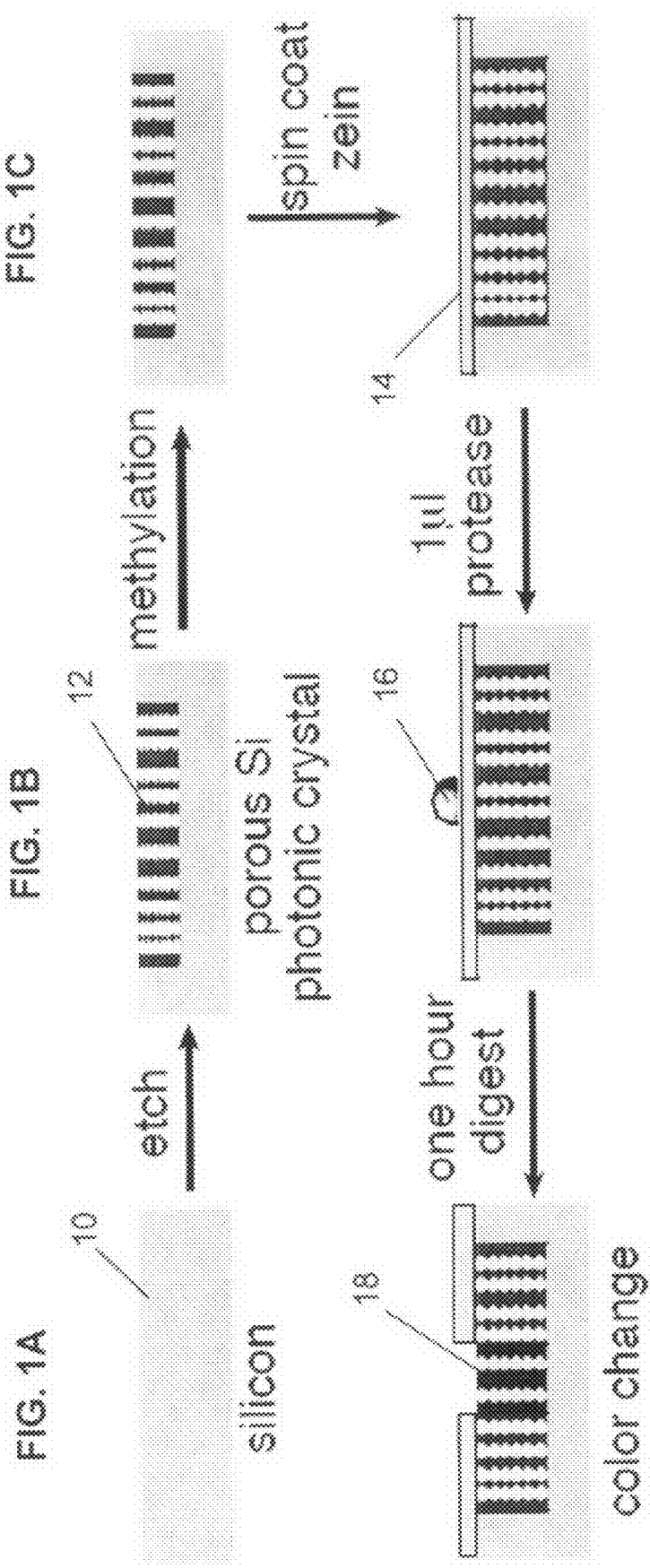
FIGS. 1A-1F schematically illustrate a preferred embodiment method of fabrication, a preferred optical sensor for chemical reaction activity, and a preferred method of detecting chemical reaction activity of the invention.

The invention provides an optical sensor for detecting chemical reaction activity. An optical sensor of the invention includes a porous photonic film that produces a predetermined spectral reflectance response. The invention can be used to detect any analyte that can degrade a substrate carried by a porous optical sensor having a predetermined optical response so long as the substrate, analyte and sample matrix are excluded from the pores prior to reaction and permit penetration of solution and/or reaction products into the pores, or a reduction in molecular weight of the film after reaction.

The film preferably has an affinity coating within its pores to attract reaction products of the substrate and the analyte. A thin substrate susceptible to reaction by at least one analyte of interest is on the surface of the thin film to block pores of the thin film. A method of detecting chemical reaction activity of the invention exposes the optical sensor to an analyte of interest. The optical sensor is subjected to light and the reflectivity spectrum of the optical sensor is monitored for a change indicative of chemical reaction activity. Monitoring can include observation for a visible change or data acquisition via instruments such as a spectrometer for monitoring for a change in interferometric reflectance spectra.

In a preferred embodiment optical sensor, the affinity coating is a methyl species grafted into pores of the porous photonic film, and serves the dual purpose of protection of the porous photonic film and attraction of reaction products. In a preferred embodiment, pores are sized to exclude the protein substrate susceptible to digestion and are sized to accept digestion products of the protein substrate susceptible to digestion. In a preferred embodiment, the porous photonic film is porous silicon.

In a preferred embodiment method of detecting chemical reaction activity, the step of monitoring the reflectivity spectrum of the optical sensor for a change indicative of chemical reaction activity can be observation for a visible color change resulting from degradation of the substrate. A visual indication can be readily apparent from a change in the color of reflection. In a preferred embodiment, the monitoring the reflectivity spectrum of the optical sensor for a change indicative of chemical reaction activity uses interferometric reflectance spectra. In a preferred embodiment, the step of subjecting the optical sensor to light and the step of sensing interferometric reflectance spectra is accomplished illuminating a spot with a bifurcated optical cable and sensing the interferometric reflectance spectra through the same optical cable.

A sensor of the invention can be used for detecting chemical reaction activity in a small, low-power chip-based system. Preferred embodiment sensors and methods use photonic films of silicon. Other materials can be used, as well, such as other semiconductors or insulators.

The porous thin films used in sensors of the invention can be formed to produce a very precise optical spectrum by control of the preparation conditions. The nanostructure provides spectral peaks that are much sharper than can be observed with molecular dyes or quantum dots. An embodiment of the invention uses color changes induced in a porous silicon photonic film as a sensitive probe of chemical reaction activity.

A preferred biosensor and method of the invention detects enzyme activity. Biosensors and methods of the invention can conduct an assay for detecting an enzyme, such as protease or cellulases and other carbohydrate-hydrolysing enzymes, in a small amount of time, e.g., 1-2 hours, whereas some conventional calorimetric assays require as long as 24 hours. No modifications to the protein being used to test for enzyme activity are necessary, as the protein can be deposited on the thin porous film, whereas a standard system such as the PDQ Protease Assay uses a cross-linked substrate matrix containing protein and dye-protein conjugate and the Athena Enzyme systems assay uses a mixture of gelatin and albumin cross-linked in the presence of sulfaniloazo-albumin with formaldehyde. Embodiments of the invention are less labor intensive as well, and require as little as 1 hour incubation at room temperature. Multiple assays may be performed on a single chip surface, whereas existing assay systems require separate vials for each assay. The color spot test of an embodiment of the invention is visible to the naked eye, as compared to typical fluorescence-based systems that require a fluorometer. Embodiments of the invention require a decreased amount of reagent (cell extract, purified enzyme, etc.). For example, an embodiment of the invention may use as little as 1 µl of assay compared to the 0.5 ml of sample required for traditional systems. An assay of an embodiment of the invention may be run at room temperature, whereas some traditional systems require 24 hour incubation at 37° C. Advantageously, the assays according to various embodiments of the invention dramatically reduces the amount of enzyme needed, and are amenable to high-throughput or in-field applications.

Embodiments of the invention include an optical biosensor for enzyme activity using a one-dimensional photonic crystal of porous silicon that is able to detect nanograms of enzyme. The principles of a preferred embodiment protease sensor and methods of the invention have been demonstrated with a porous Si layer that is coated with a thin substrate of zein, a natural hydrophobic protein from maize. Proteolytic cleavage produces small fragments that infiltrate the pores of the photonic film, producing a readily observable color change.

The invention can be used to detect any analyte that can degrade a substrate carried by a porous optical sensor having a predetermined optical response so long as the substrate, analyte and sample matrix are excluded from the pores prior to reaction and permit penetration of solution and/or reaction products into the pores, or a reduction in molecular weight of the porous film after reaction. Example analytes include enzymes, such as proteases, and other catalytic and noncatalytic molecules that cause a degradation, cleavage, or other decrease in molecular weight of the substrate susceptible to reaction. Example substrates susceptible to reaction include proteins, RNAase, DNAase, or hydrolytic enzymes. The affinity coating can be a hydrophobic coating, for example, or an appropriate one of a DNA, RNA, organic oligomers or polymers, metal or nonmetal oxides, or metals.

Preferred embodiment sensors and sensing methods will now be discussed with reference to the drawings. Drawings presented schematically will be understood by artisans with reference to the accompanying description here. Drawings are not to scale, and features may be exaggerated for purposes of illustration. Broader aspects of the invention will be recognized by artisans through the illustrated preferred embodiments.

FIGS. 1A-1F schematically illustrate a preferred embodiment method of fabrication, a preferred chemical reaction activity sensor, and a preferred method of detecting chemical reaction activity of the invention. In accordance with one embodiment of the invention, fabrication of a photonic film involves anodic etching of a p-type, boron-doped silicon wafer 10 polished on the (100) face (FIG. 1A), that produces a photonic thin film 12. As an example, a sinusoidal etch waveform produces a film with an alternating porosity gradient in the <100> direction that acts as a one-dimensional photonic crystal; the film displays a distinct optical diffraction peak in the white light reflectivity spectrum. The wavelength of the peak is determined by the period of the waveform used in preparation.

Other embodiments can include more complicated optical spectrums and can use other semiconductors or insulators. Strategies for encoding porous films are discussed in the background of this application. Various codes and porous sensing film structures can be used in the invention, and artisans are referred to the background and the art for techniques for forming porous layers for use in a protease activity biosensor of the invention. Particular preferred porous thin film formation strategies are disclosed in the following U.S. Published Applications: 20060236436, published Oct. 19, 2006 and entitled Nanostructured Casting of Organic and Bio-Polymers in Porous Silicon Templates; 20060105043, published May 18, 2006 and entitled Porous Nanostructures and Methods involving the same; 20050042764, published Feb. 24, 2005 and entitled Optically Encoded Particles; 20050009374, published Jan. 13, 2005 and entitled Direct Patterning of Silicon by Photoelectrochemical Etching; 20040152135, published Aug. 4, 2004 and entitled Porous Semiconductor-Based Optical Interferometric Sensor; and 20030146109, published Aug. 7, 2003 and entitled Porous thin film time-varying reflectivity analysis of samples. Also see U.S. Pat. Nos. 6,897,965, 6,720,177, and 6,248,539, which disclose semiconductor based optical interferometric sensors and discuss fabrication of the same.

The porous Si layer is then coated with a chemical coating, e.g. it is made hydrophobic The Si layer can be made hydrophobic, for example, if it is methylated to impart stability and hydrophobicity using an electrochemical grafting procedure. FIG. 1C. The methyl species attaches to the inner pore walls of the photonic thin film 12. A thin protein substrate 14 susceptible to chemical reaction, e.g., digestion by a protease of interest, is then formed on the photonic film 12.

As an example, as used in experiments to demonstrate the invention, a solution of the hydrophobic, naturally occurring protein zein in methanol (10 mg/ml) is spin-coated onto the methylated porous silicon film 12 creating an even protein coating. Zein tends to form multilayered films on silicon surfaces through molecular and electrostatic interactions. Preferably, the pores in the porous film 12 are sized to exclude the protein that is used to form the thin protein substrate 14 but are large enough to accept digestion products of the protein substrate/protease reaction. Optical changes can be apparent, however, from any degradation of the substrate. The invention can be used to detect any analyte that can degrade a substrate carried by a porous optical sensor having a predetermined optical response so long as the substrate, analyte and sample matrix are excluded by the pores prior to reaction and permit penetration of solution and/or reaction products into the pores, or a reduction in molecular weight of the porous film after reaction. Example analytes include enzymes, such as proteases, and other catalytic and noncatalytic molecules that cause a degradation, cleavage, or other decrease in molecular weight of the substrate susceptible to reaction. Example substrates susceptible to reaction include proteins, RNAase, DNAase, or hydrolytic enzymes. The affinity coating can be a hydrophobic coating, for example, or an appropriate one of a DNA, RNA, organic oligomers or polymers, metal or nonmetal oxides, or metals.

In experimental films, for example, pores in a photonic crystal film were approximately 10 nm, which prevents the protein zein from infiltrating the crystal film 12 to a significant extent. In experiments, the presence of a zein coating was observed as a thin substrate that does not obscure the reflectivity spectrum of the underlying photonic crystal.

An assay is carried out by addition of a small drop of solution 16 containing analyte, e.g., active protease, such as pepsin or pronase E, for example, which digests the protein substrate exposing a small portion 18 of the thin film 12 and changing its reflectivity spectrum due to the infiltration of digestion products of the protease/protein reaction. Infiltration of proteolytic cleavage products (digestion products) to the photonic film leads to a color change that is readily observable to the unaided eye. This can be used to signal the detection of the protease of interest.

In addition, levels of analyte, e.g., protease can be determined. In preferred embodiments, the reflectivity spectrum of the sensor is taken before and after exposure to fluid that may contain the protease of interest. In a preferred embodiment, a spot where the drop of solution 16 is applied is illuminated with a dual fiber optical probe that also then picks up the reflection spectrum, which is measured, for example with a spectrometer. Peaks of the interferometric reflectance spectra of the sensor and their shift can provide information about the presence and quantity of the protease of interest. With the thin film, the assay can be completed in a short time, e.g., 1-2 hours.

A simple protease activity assay method of the invention can detect pmol quantities of protease at room temperature, as indicated by experimental data. A silicon chip-based system is compatible with a high-throughput array configuration important for many biotechnological applications, such as medical diagnostics, quality control testing, enzyme purification, cell extract assays, or drug discovery. Although demonstrated with the maize derived protein zein, a wide variety of native protein substrates, including those targeted by DNases and RNases, can be used to detect other enzymes of interest.

Experiments

Experiments will now be discussed. Experiments have been conducted to verify the principles of the invention. The invention is not limited to the experimental devices and methods, as artisans will recognize that commercially fabricated devices and optimizations can be used to optimize sensing results using sensors and methods of the invention. Preferred fabrication techniques will also be discussed, and artisans will recognize various commercial fabrications based upon the description that are within the scope of the invention. Artisans will appreciate additional embodiments and broader aspects of such embodiments from the following discussions of experiments.

In the experiments, a porous crystal silicon film biosensor was used. The protein substrate was zein. Changes in refractive index of the porous silicon layer as protein fragments (n=1.42) replace air (n=1) in the pores result in a red shift of the reflectivity peak, producing an observable color change.

Since buffer solutions (typically n=1.34) also have a higher refractive index than air, it is desirable to modify the photonic crystal with hydrophobic functional groups that exclude buffer from the porous structure unless the protease digestion products are present. This was accomplished in the experiments by grafting of methyl groups to the porous silicon layer by electrochemical reduction of $CH_3I$ in acetonitrile. After methyl grafting, the position of the reflectivity peak red shifts when a drop of buffer solution containing protein digestion fragments is placed on the film. Pure buffer solution produces no significant change in color, on the other hand indicating that the amino acid digestion products act as surfactants to facilitate solution infiltration.

When the zein layer is added to the porous Si film, the reflectance peak red-shifts by only a small amount indicating that the intact protein is effectively excluded from the film.

A secondary purpose of the methylation step is to improve the chemical stability of the porous Si layer. As-prepared porous Si corrodes rapidly in buffer solutions; the methylation step stabilizes the porous Si layer such that no significant degradation of the spectral properties occurs on the timescale of the present experiments.

The zein overcoating effectively prevents infiltration of aqueous solutions and their contents until the protein substrate is digested by the action of a protease. Addition of a 1 µl drop of aqueous buffer containing pepsin to the top surface of the zein substrate produces a visibly detectable clear color change in the photonic crystal for pepsin quantities as low as 7 pmol, and some color change was indicated at 3.6 pmol. This was observed with a series for active protease pepsin where drops contain pepsin quantities of 0, 1.8, 3.6, 7.2, 14.3, and 28.6 pmol in buffer solution (pH 2.0) were placed on different parts of a zein-coated photonic crystal biosensor of the invention and allowed to react. The biosensor film was 1.2 cm in diameter. A very distinct color change of the photonic crystal from green to red was observed for quantities of pepsin as low as 7 pmol, and some color change was visible for the 3.6 pmol drop.

Figure 2:
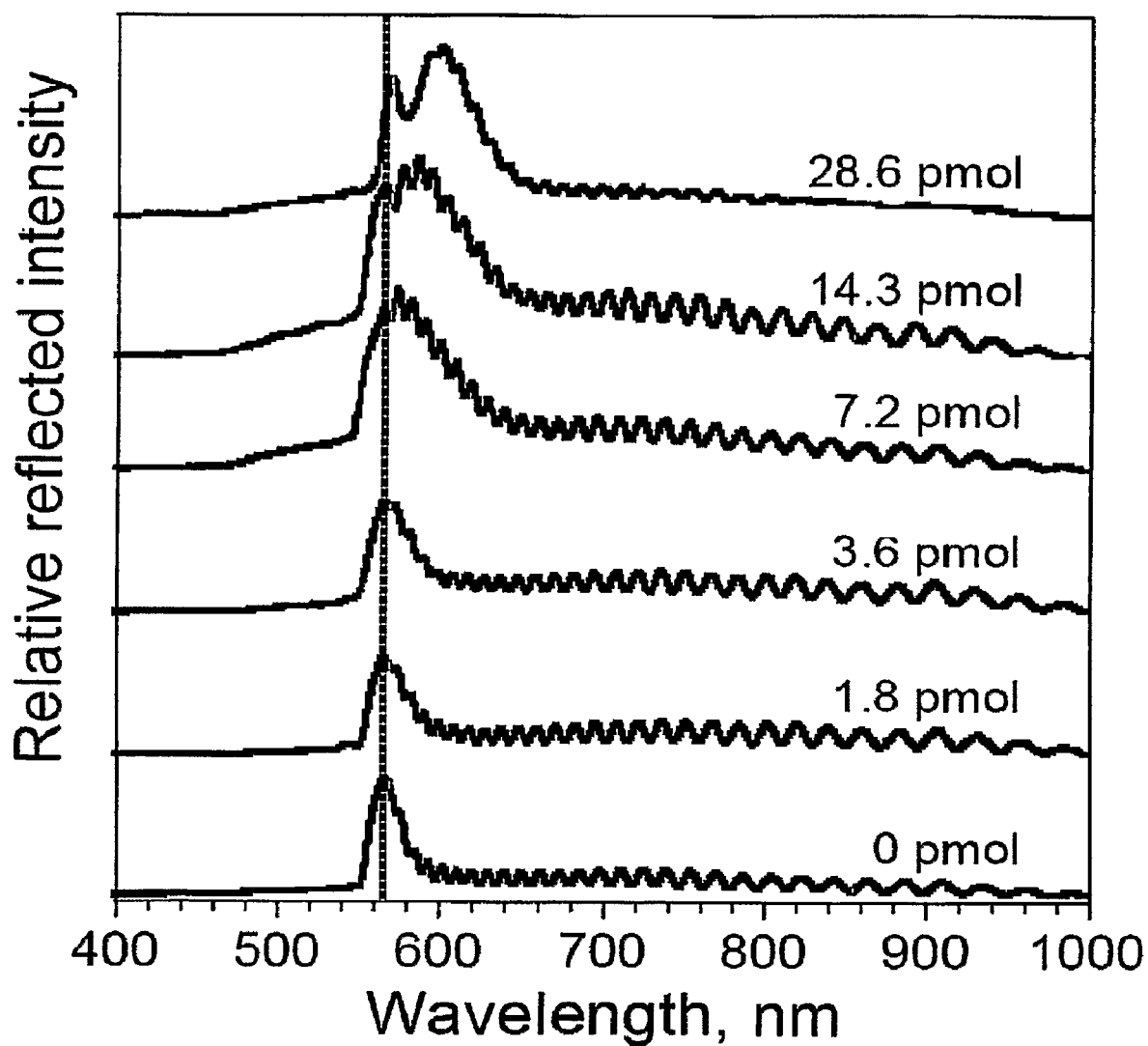
FIG. 2 is a plot of experimental data showing reflectivity spectra taken from spots on a zein-coated protease activity biosensor of the invention resulting from addition of the indicated quantities of pepsin.

The reflectivity spectrum allows quantification of protease activity, as shown in FIG. 2. Reflectivity spectra obtained from zein-coated porous photonic crystals display a single strong peak corresponding to the stop band of the empty (air-filled) photonic crystal. Etalon fringes due to Fabry-Perot interference in the porous Si film are also apparent in the spectra. Action of pepsin on the zein substrate results in the appearance of a second peak, red-shifted from the first. This new peak is assigned to regions of the porous Si photonic crystal that have become filled with protease digestion products. Introduction of protein fragments produces a red-shift in the photonic peak due to an increase in the total refractive index of the porous film. The Bruggemann effective medium model predicts that the peak shift will be larger in spectra of samples containing larger quantities of protein fragments. Consistent with this, samples that have been exposed to higher concentrations of protease show greater spectral shifts. For samples treated with 1 µl drops containing greater than 7.2 pmol of pepsin, the spectra display two distinct peaks and the red shift is clearly visible by eye. For samples exposed to concentrations of pepsin smaller than 7.2 pmol the spectral shift can be resolved by applying a double Gaussian fit to the spectral profile, allowing reliable detection of as little as 2 pmol of pepsin.

Each spectrum in FIG. 2 corresponds to a spot in the dilution series discussed above that used the pepsin quantities of 0, 1.8, 3.6, 7.2, 14.3, and 28.6 pmol. A peak assigned to regions of the porous Si photonic crystal that have become infiltrated with protease digestion products appears to the low energy side of the original spectral band. The original peak (unfilled with digestion products) indicated with a vertical dashed line. Spectra are offset along the y-axis for clarity. For protease quantities in excess of 7.2 pmol, the peak corresponding to the presence of digestion products (at longer wavelength in the reflectivity spectrum) is more intense than the shorter wavelength peak. As with the correlation of spectral shift to protease concentration, the observed increase in peak intensity is consistent with an increase in the quantity of digestion fragments produced by the larger concentration of protease.

Figure 3:
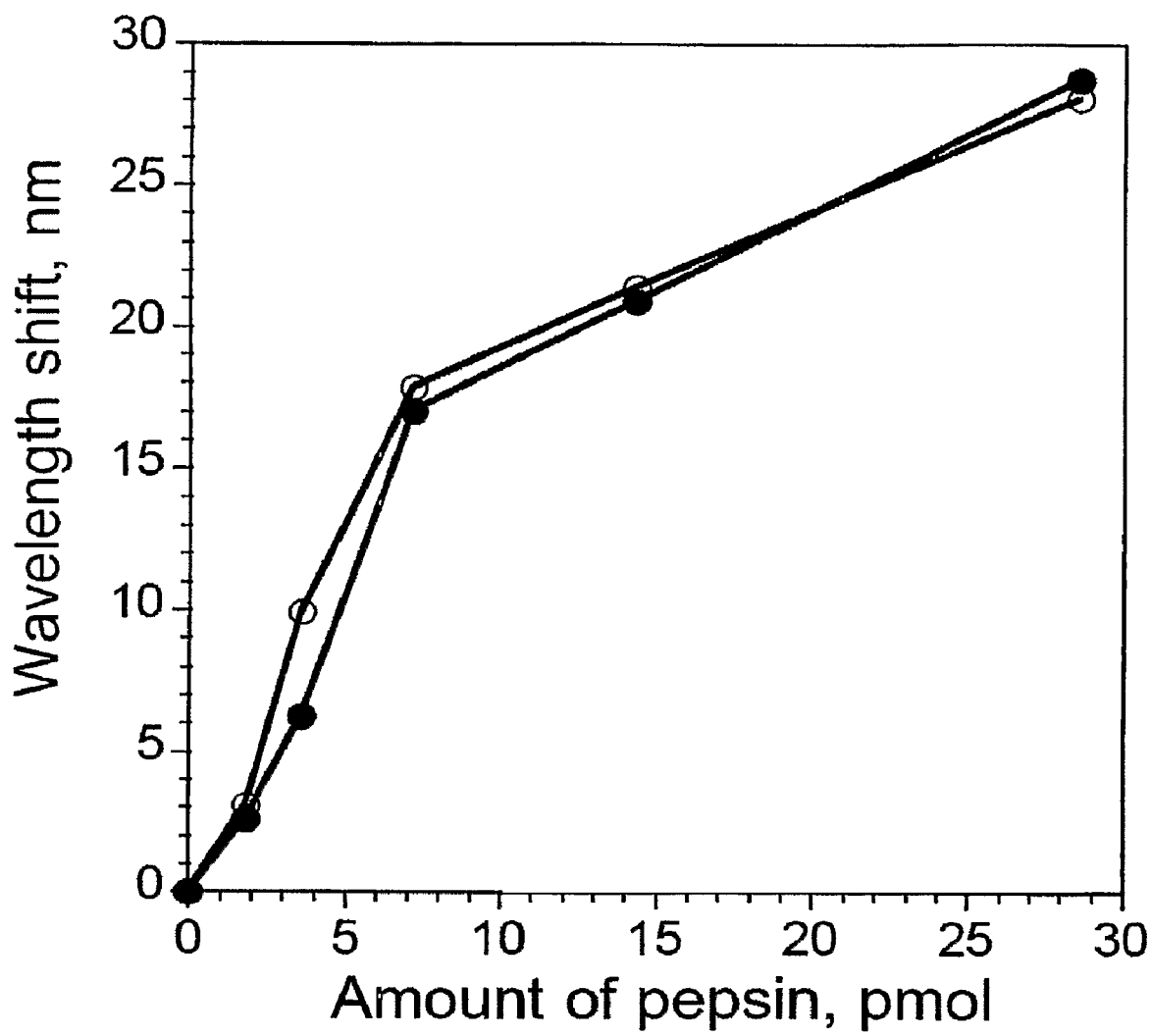
FIG. 3 is a plot of experimental data showing a red shift of photonic peak resulting from action of pepsin on protease activity biosensor of the invention as a function of the amount of pepsin added.

FIG. 3 shows the red shift of the photonic peak resulting from action of pepsin on the zein substrate as a function of the amount of pepsin added. The magnitude of the spectral red shift is calculated as the separation of the two peaks observed in each spectrum of FIG. 2. The two peaks correspond to regions of the film that are either empty (shorter wavelength) or that contain protease digestion products (longer wavelength). Peak positions are determined from a fit of the spectrum to a double Gaussian function. Data from replicate experiments on two different porous Si film samples are shown (open and closed circles).

Several control experiments were performed, following the same protocol as was used with the active pepsin assay described above. In one control experiment, different parts of the photonic crystal silicon film not including a protein target film for protease reaction was tested. The spots included (a) a solution of zein fragments, generated by digestion in a pH 2.0 buffer solution containing 1 mg/ml zein with 1 mg/ml of the protease pepsin (digestion for 1 h at room temperature); (b) a pH 7.4 PBS buffer; (c) Film spotted with pH 2.0 buffer; (d) deionized water; (e) a pH 10.0 buffer; (f) the active protease pepsin (1 mg/ml) in pH 2.0 buffer. All spots used a 1 μl aliquot of solution, and the incubation protocol was the same as used above. Only the spot (a) with the digested zein fragments produced a clear visible color change and a strong red spectral shift.

Figure 4:
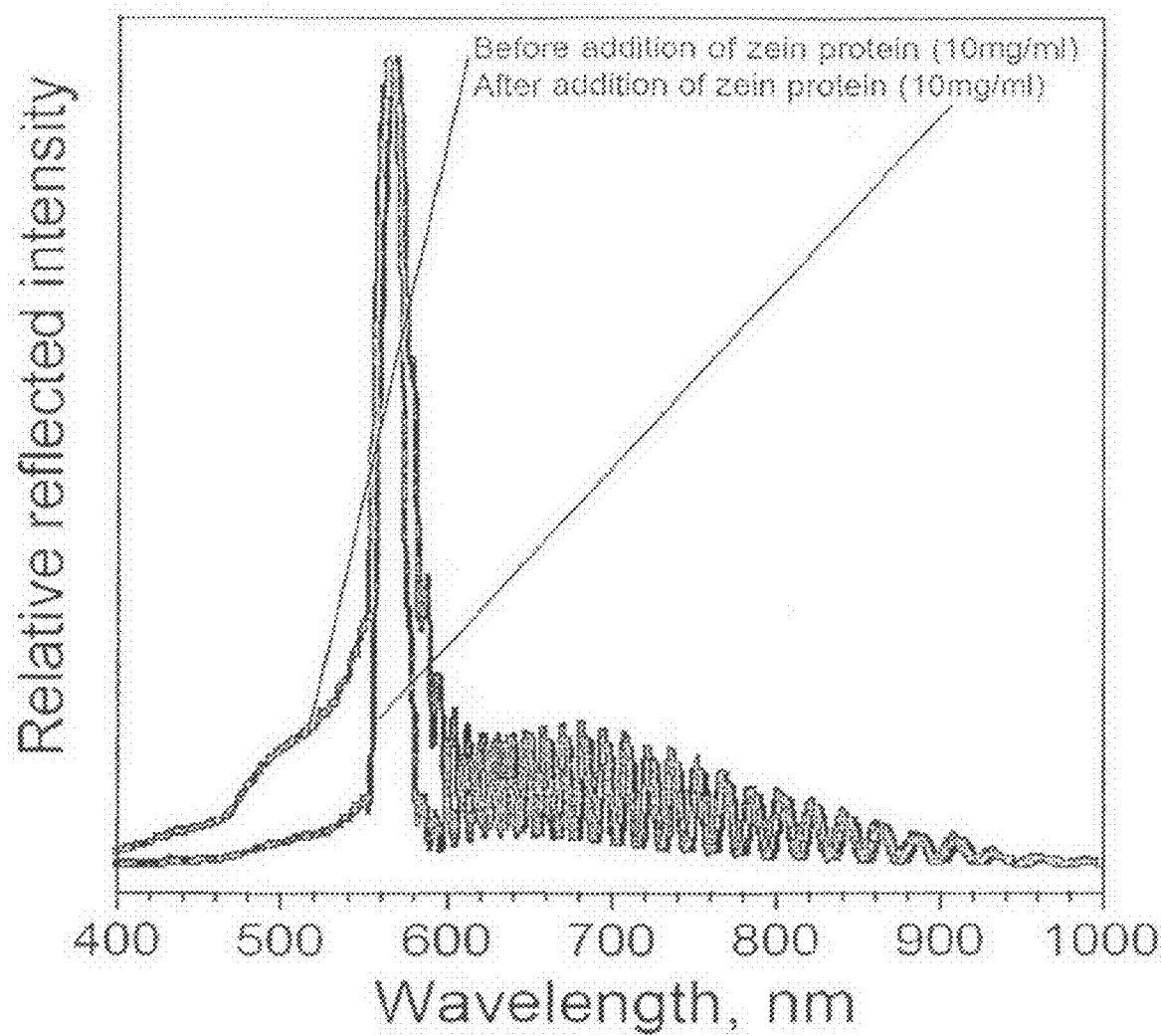
FIG. 4 is a plot of experimental data showing the reflectance spectrum taken from the same spot on a porous protease activity biosensor of the invention before and after addition of zein coating.

A 1 μl drop of the pH 2 buffer solution placed on the zein-methylated film produces no visible color change and a spectral red shift of <4 nm, as indicated in FIG. 4. The amount of red shift being less than 4 nm indicates that the zein protein does not infiltrate the pores appreciably.

Figure 5:
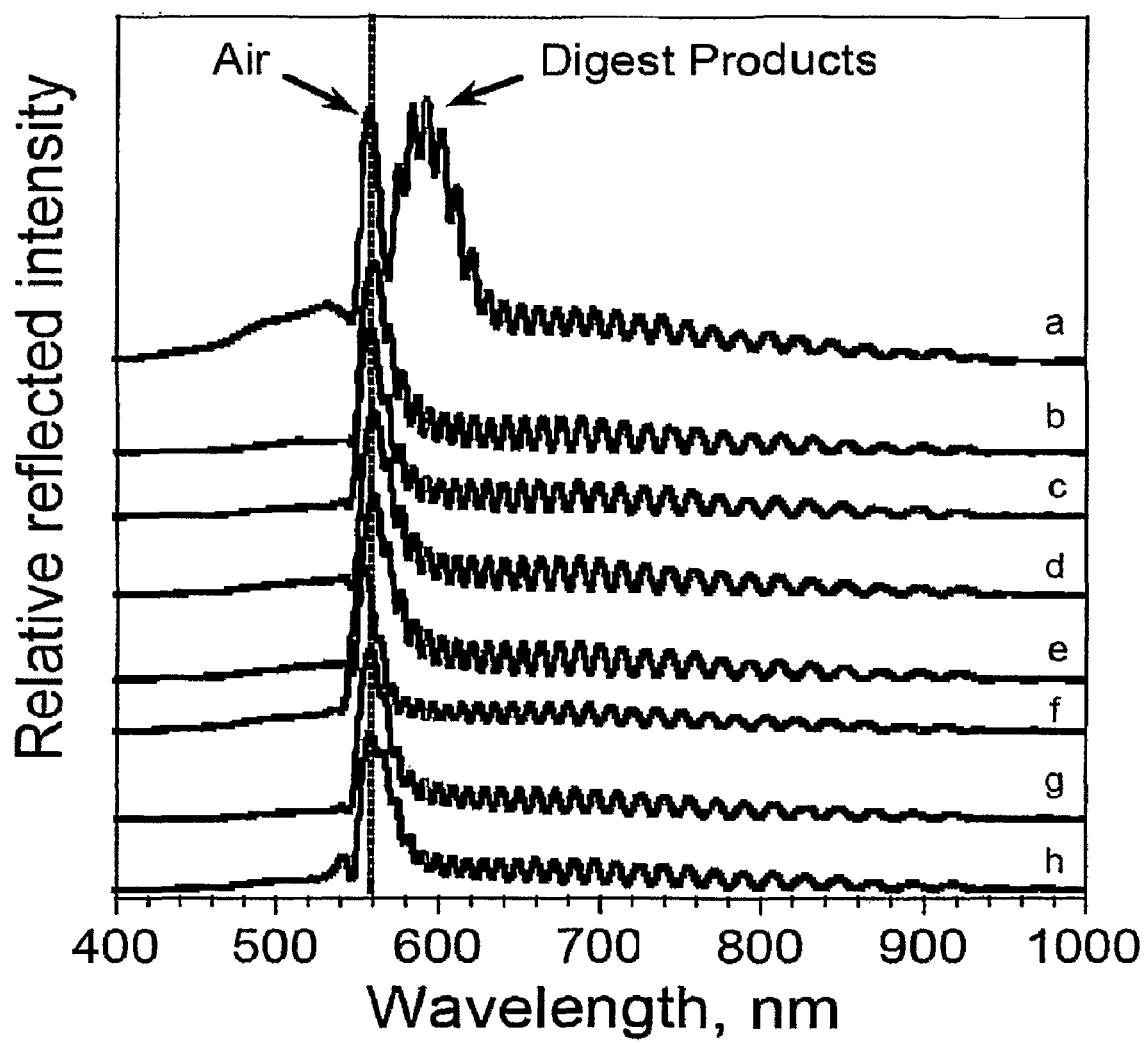
FIG. 5 is a plot of experimental data showing the reflectance spectra resulting from the action of a number of reagents on a protease activity biosensor of the invention, after completion of the reaction and drying of the solutions.

Controls using heat-denatured pepsin, active pepsin in pH 10 buffer (where pepsin has minimal activity) or active pepsin in a solution containing the inhibitor (pepstatin) produced negligible changes in the observed color and peak positions. A number of different drops were placed at various locations of a biosensor consistent with the experimental sensors discussed above. The drops included: (a) 1 μl solution of active protease pepsin (1 mg/ml) in pH 2.0 buffer; (b) plain pH 2.0 buffer; (c) de-ionized water; (d) pH 7.4 PBS buffer; (e) a pH 2.0 buffer solution containing 1 mg/ml of pepsin that had been inactivated by treatment with the inhibitor pepstatin (1:1 pepsin:pepstatin); (f) a pH 10.0 buffer solution containing 1 mg/ml of pepsin (pepsin is inactive at pH 10); (g) a pH 2.0 buffer solution containing 1 mg/ml of pepsin that had been inactivated by heat treatment; and (h) untreated spot used to obtain the background spectrum. All spotting experiments used a 1 μl aliquot of solution, and the incubation protocol was the same as a described above. The spectra are shown in FIG. 5, which is offset along the y-axis for clarity. The spot exposed to activated pepsin (spot (a)) displays the red shifted peak at 595 nm, characteristic of infiltration of protease digestion products.

A spotting experiment was also conducted with the protease pronase E, which produced similar results to those observed with pepsin, despite the lower activity of pronase E. Only spots with active pronase E showed a visible color change. The Pronase E used in these experiments has activity less than the activity of Pepsin (4 unit/mg solid vs. 150 unit/mg solid, respectively). A unit of pronase E is defined by hydrolysis of casein to produce a color equivalent to 1.0 μmole (181 μg) of tyrosine per min at pH 7.5 at 37° C. (color by Folin-Ciocalteu reagent). One unit of pepsin will produce a change in absorbance at 280 nm (ΔA280) of 0.001 per min at pH 2.0 at 37° C., measured as the TCA-soluble products using hemoglobin as substrate. (Final volume 16 ml. Light path=1 cm).

Sample preparation in experiments used anodic etching of degenerate p-type, boron-doped, (100)-oriented silicon wafers (Siltronix, Inc.) with resistivity <2 mΩ-cm in a 3:1 (v/v), 49% aqueous HF/ethanol (EMD Biosciences) solution. A Teflon etch cell that exposed 0.58 cm$^2$ of the silicon wafer was employed. The current density was modulated with a sinusoidal waveform ranging between 17-78 mA/cm$^2$, with a period of 9 s for 60 cycles, generating a multilayered optical structure known as a Rugate filter. Methylation of the porous Si film was achieved by passing a cathodic current density of 6.5 mA/cm$^2$ through the porous Si film immersed in 3.5 ml of an electrolyte solution containing 0.5 M iodomethane (99+%, Alfa Aesar) and 0.2 M anhydrous lithium iodide (99%, Arcos Organics) in anhydrous acetonitrile (Fisher Chemicals) for 2 min22. Samples were illuminated with 200 mW/cm$^2$ of white (tungsten lamp) light during the methyl grafting procedure. The electrolyte solution was removed and the sample rinsed sequentially with glacial acetic acid, acetonitrile, and ethanol. A 200 μL aliquot solution of 10 mg/ml zein (Sigma) in methanol (Fisher Chemicals) was then spin-coated onto the photonic crystal film.

For the enzymatic digestion procedure, active pepsin solutions were prepared by adding pepsin A (150 units/mg solid, Sigma) to a prepared 10 mM pH 2.0 buffer containing phosphoric acid (99.9%, Aldrich) sodium phosphate monohydrate (enzyme grade, Fisher chemicals), HCl (EM Science) and deionized water. Heat-inactivated pepsin solution was obtained by heating the above solution to 100° C. for 5 min. The pH-inactivated pepsin solution was prepared in pH 10.0 buffer (Fisher chemicals). Pepstatin inhibitor (Sigma) was dissolved in 9:1 methanol: acetic acid (v/v) and mixed with activated pepsin solution. Pronase E (Type XIV, ~4 units/mg solid, powder, Sigma) was added to Dulbecco's phosphate buffered saline solution containing calcium chloride and magnesium chloride (Sigma). Controls included deionized water and Dulbecco's phosphate buffered saline. Aliquots of 1 μl of the pepsin solutions or controls were deposited onto the zein-coated porous Si photonic crystal by microliter syringe. The sample was maintained in a humid chamber at room temperature for one hour, after which the sample was removed to the laboratory air and the solution allowed to evaporate in air for 10-20 min. before performing the spectroscopic or microscopic measurements.

Interferometric reflectance spectra were obtained with an Ocean Optics S-2000 CCD spectrometer fitted with a microscope objective lens. The lens was coupled to a bifurcated fiber optic cable such that both illumination and detection of reflected light could be performed on the same spot on the sample, along an axis coincident with the surface normal. A tungsten light source was input to one of the two fiber ends and focused onto the center of the sample surface with a spot size of approximately 2 mm$^2$. Reflectivity data were recorded in the wavelength range 400-1000 nm, with a spectral acquisition time of 100 ms. Spectral red shifts were determined from Gaussian fits to the spectral peaks.

The function used to fit each spectrum was a sum of two Gaussian Curves $f(x)=Y1+A1*\exp(-((x-\text{offset1})/\text{width1})^2)+A2*\exp(-((x\text{offset2})/\text{width2})^2)$ where Y1 is the baseline offset, A1 is the amplitude, offset1 is the wavelength maximum, and width1 represents the peak width of Gaussian #1. A2, offset2, and width2 represent the corresponding values for Gaussian #2. A non-linear least-squares fitting routine involving iterative minimization of the sum of the chi-squared values, using the Levenberg-Marquardt algorithm, was applied (IGOR PRO program, Wavemetrics, inc.). The parameter Y1 was set as a constant in the fitting routine. Initial input values were obtained from a single Gaussian fit of the "in air" spectral peak (obtained before addition of protease). The quantity (offset2−offset1) is what is plotted in FIG. 3, representing the total red shift upon addition of a given amount of protease.

While specific embodiments of the present invention have been shown and described, it should be understood that other modifications, substitutions and alternatives are apparent to one of ordinary skill in the art. Such modifications, substitutions and alternatives can be made without departing from the spirit and scope of the invention, which should be determined from the appended claims.

Various features of the invention are set forth in the appended claims.

The invention claimed is:

1. An optical sensor for detecting chemical reaction activity, the sensor comprising:
    a porous photonic film that produces a predetermined spectral reflectance response; and
    a thin substrate blocking the pores of the porous photonic film that is susceptible to reaction by at least one analyte of interest on the porous photonic film.

2. The optical sensor of claim 1, wherein inner pore walls of said porous photonic film have a coating with an affinity for reaction products of said substrate and said porous photonic film.

3. The optical sensor of claim 1, wherein inner pore wall of said porous photonic film have a protective coating comprised of an organic species grafted into the pores of the porous photonic film.

4. The optical sensor of claim 3, wherein pores of the porous photonic film are sized to exclude the analyte.

5. The optical sensor of claim 1, wherein pores of the porous photonic film are sized to exclude the analyte.

6. The optical sensor of claim 4, wherein the pores of the porous photonic film are sized to accept reaction products of the substrate.

7. The optical sensor of claim 6, wherein the porous photonic film comprises porous silicon.

8. The optical sensor of claim 6, wherein the porous photonic film comprises a photonic crystal film of porous silicon.

9. The sensor of claim 1, wherein the analyte comprises an enzyme.

10. The sensor of claim 9, wherein the analyte comprises a protease.

11. The sensor of claim 9, wherein the substrate comprises a protein substrate.

12. The sensor of claim 1, wherein the analyte comprises a catalytic or reactive molecule.

13. The sensor of claim 1, wherein the analyte comprises one of catalytic and noncatalytic molecules that cause a degradation, cleavage, or other decrease in molecular weight of the substrate.

14. The sensor of claim 13, wherein the substrate susceptible to reaction comprises one of RNA, DNA, or the macromolecular substrate of a hydrolytic enzyme.

15. The sensor of claim 14, wherein the coating with an affinity comprises one of DNA, RNA, organic oligomers or polymers, metal or nonmetal oxides, or metals.

16. A method of detecting chemical reaction activity, the method comprising steps of:
    exposing an optical sensor according to claim 1 to an analyte of interest;
    subjecting the optical sensor to light; and
    monitoring the reflectivity spectrum of the optical sensor for a change indicative of chemical reaction activity.

17. The method of claim 16, wherein the step of monitoring comprises observing a visible color change resulting from infiltration of digestion or degradation products of the substrate into the pores of the porous photonic film.

18. The method of claim 16, wherein the step of monitoring comprises sensing interferometric reflectance spectra.

19. The method of claim 18, wherein the step of subjecting the optical sensor to light and the step of sensing interferometric reflectance spectra comprise illuminating a spot with a bifurcated optical cable and sensing the interferometric reflectance spectra through the same optical cable.

* * * * *